United States Patent [19]
Williams

[11] Patent Number: 5,740,861
[45] Date of Patent: Apr. 21, 1998

[54] REPLACEABLE CONSUMABLE EROSION DETECTOR

[75] Inventor: Michael R. Williams, Houston, Tex.

[73] Assignee: FMC Corporation, Chicago, Ill.

[21] Appl. No.: 646,820

[22] Filed: May 21, 1996

[51] Int. Cl.$^6$ ............................ E21B 47/10; G01N 15/06
[52] U.S. Cl. ............................ 166/66; 73/86; 166/75.11
[58] Field of Search ........................ 166/53, 75.11, 166/66, 250.11; 73/86, 61.71, 61.73, 152.18, 152.42

[56] References Cited

U.S. PATENT DOCUMENTS

| | | |
|---|---|---|
| 2,994,778 | 8/1961 | Marsh ............................ 73/86 |
| 3,639,876 | 2/1972 | Wilson ............................ 73/86 X |
| 3,753,257 | 8/1973 | Arnold ............................ 166/66 X |
| 4,131,815 | 12/1978 | Boatright ............................ 73/152.18 |
| 4,389,877 | 6/1983 | Lacey ............................ 73/86 X |
| 4,768,373 | 9/1988 | Spencer ............................ 73/86 |
| 4,779,453 | 10/1988 | Hopenfeld ............................ 73/86 |
| 5,221,677 | 6/1993 | Sargeant et al. ............................ 73/61.71 |
| 5,571,955 | 11/1996 | Beavers et al. ............................ 73/86 |

*Primary Examiner*—Hoang C. Dang
*Attorney, Agent, or Firm*—Henry C. Query, Jr.

[57] ABSTRACT

The present invention is directed to a detector for the detection of abrasive material being carried by fluid passing through a wellhead, the detector including an erosion block having a passage therein and a bore intercepting the passage; a probe which is inserted into the bore of the erosion block, this probe having a contact zone exposed to the passage when the probe is inserted in the bore and a first bore extension inboard of the surface of the contact zone which communicates with a first bore; and a first pressure transducer provided for sensing pressure in the first bore and in the first bore extension connected thereto; the pressure transducer providing an electrical output indicative of a change in pressure in the first bore and being electrically coupled to a device which is responsive to the electrical output of the first pressure transducer.

18 Claims, 4 Drawing Sheets

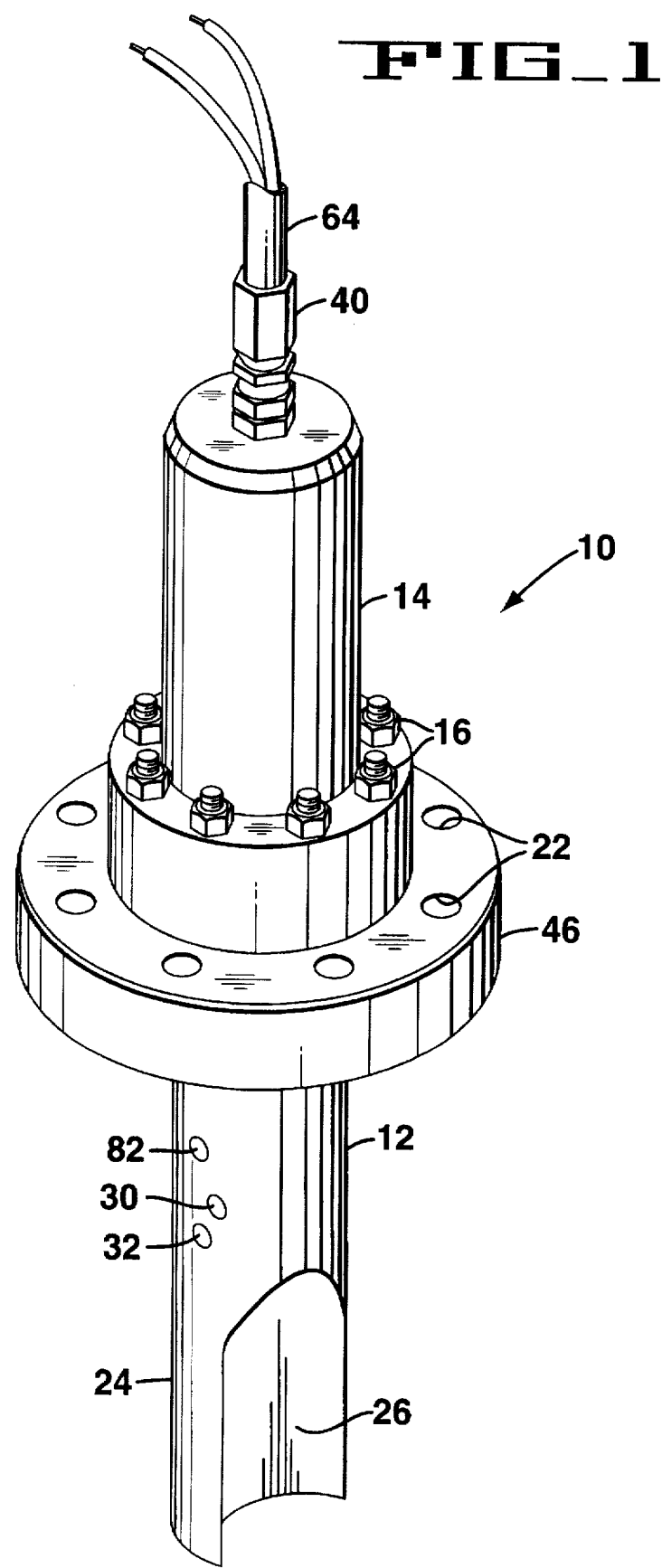
FIG_1

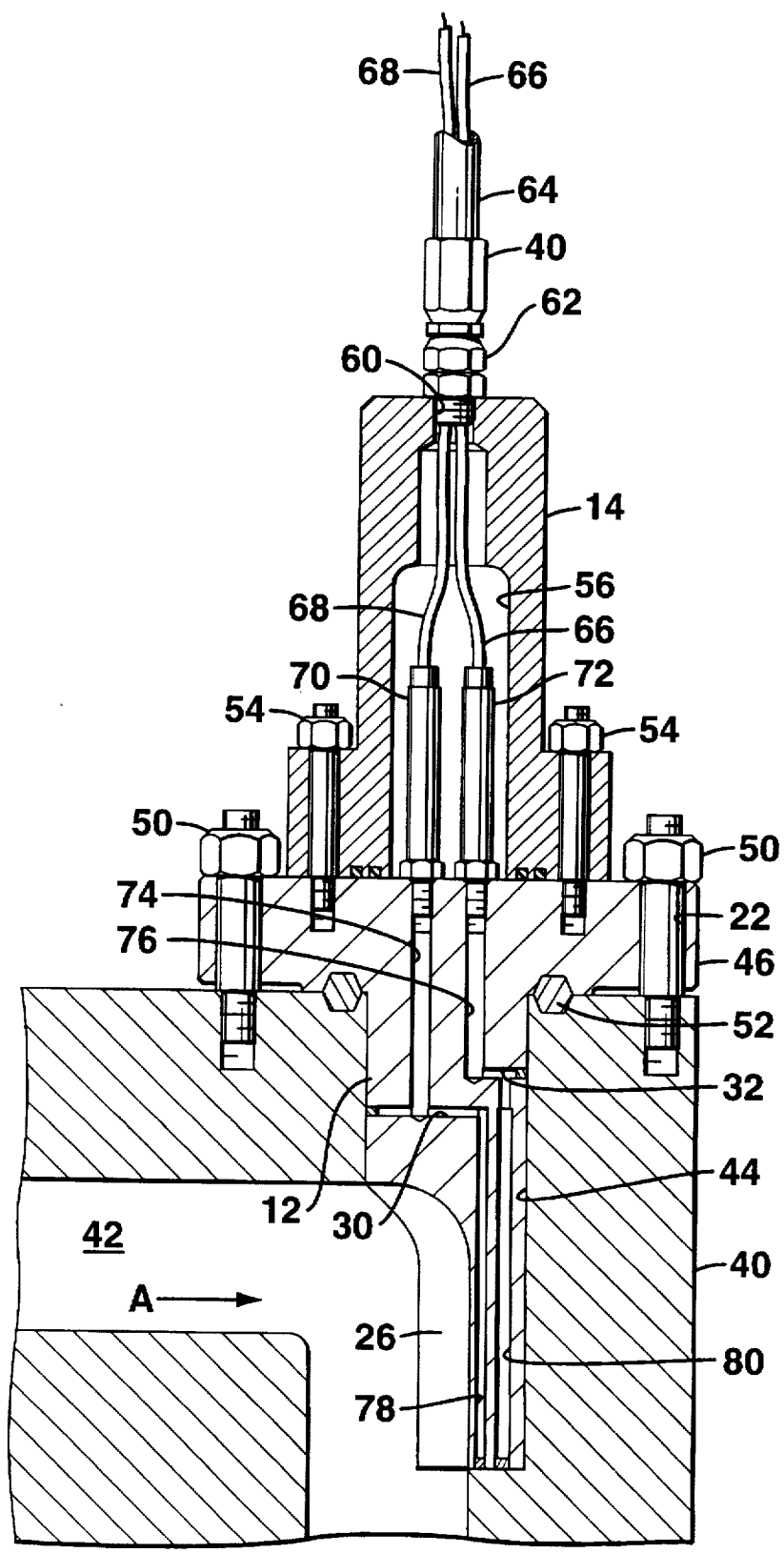
FIG_2

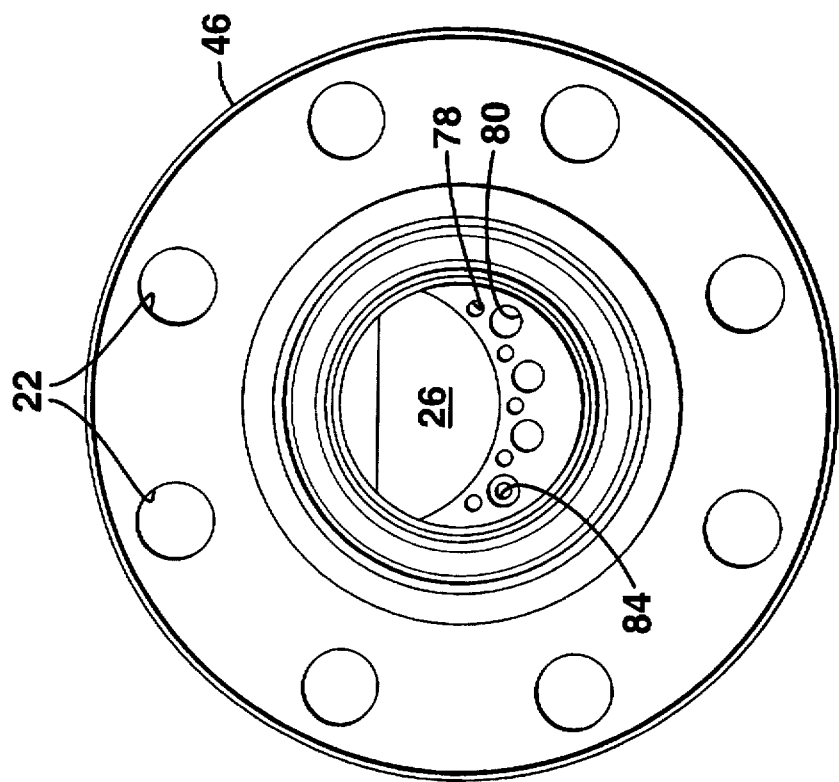
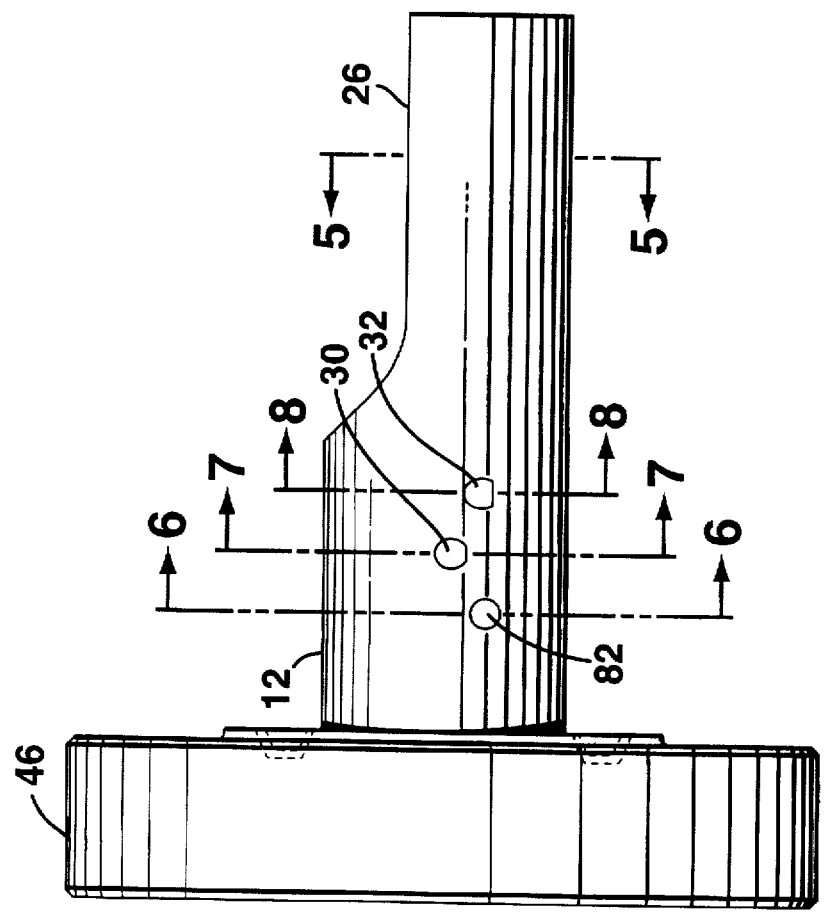

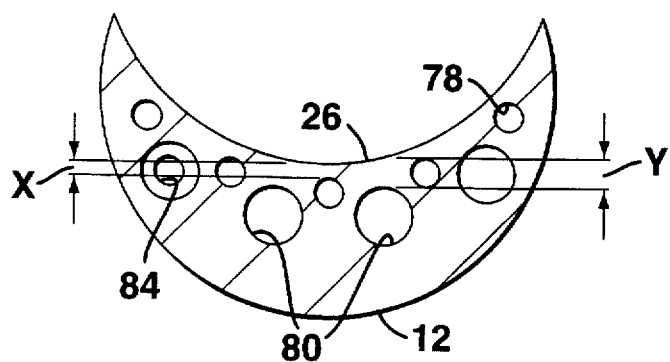
FIG_5
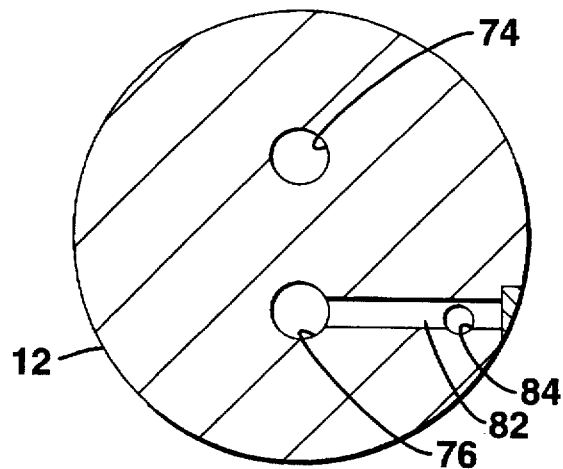
FIG_6
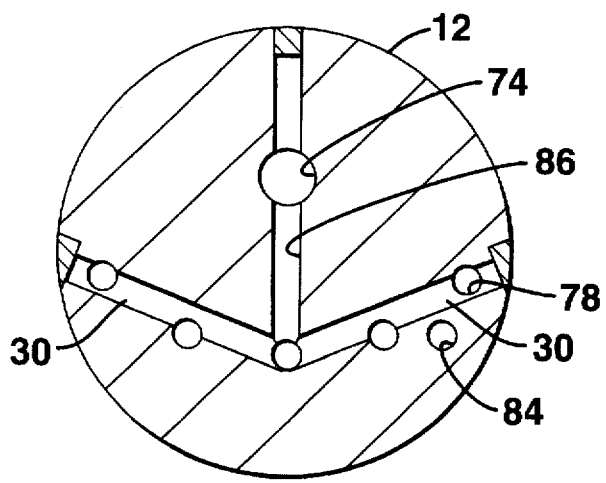
FIG_7
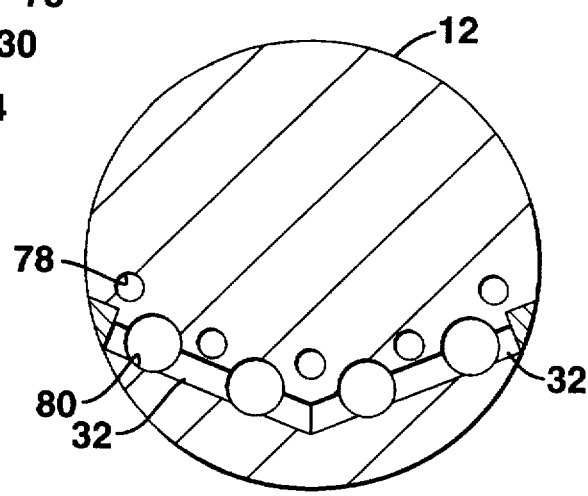
FIG_8

REPLACEABLE CONSUMABLE EROSION DETECTOR

BACKGROUND OF THE INVENTION

1. Field of the Invention

This invention has to do with apparatus for use in oil and gas well completion equipment and specifically to a method of detecting sand in a stream of gas being extracted from a well. The detection is made possible by means of a consumable apparatus, namely a probe having an erodable contact zone that is exposed to the stream of gas at the wellhead.

2. Description of the Prior Art

It has been known that sand or other abrasive materials in a gas stream have very serious effects on the plumbing systems of wellhead equipment. Traditionally, if sand were found in a gas stream it was found once the gas had traveled from the wellhead to a collection point remote from the wellhead. With the discovery of the sand the well would be shutdown to correct the problem by well known downhole remedial measures. Sometimes however the time it took to discover the problem was too long to prevent damage to the wellhead due to the sand caused erosion and the ablation of the interior metal surfaces of valves, pipes, elbows, sensors and other wellhead and fluid transportation systems.

One method of sensing erosion in a well conduit was the use of a probe that intruded into the stream of fluid being transported by the pipe or other plumbing. These detectors are electrical devices that apparently change their electrical signal output as they are eroded away. The difficulty with these devices is that they are positioned in the interior of the conduit and may provide an impediment to fluid or items traveling through the conduit or may otherwise be subjected to damage not a function of erosion.

Another method of detecting wear is to have a special spool piece in the line. As the interior wall of the spool piece is eroded the diameter of the interior will be measured and when the wear is critical responsive action could be taken. The disadvantage of this type of detector is that the replacement of the spool piece is difficult as two end flanges need to be uncoupled and reconnected with the new spool piece.

SUMMARY OF THE INVENTION

The invention presented here is designed to give an early warning to well operators that there is sand being extracted from the well with gas product. The early warning is conveyed to the operator by means of a signal emanating from a pressure transducer connected to a special fitting at the wellhead. The pressure transducer is in communication with a normally closed chamber of a given static pressure. In the event that the normally closed chamber is breached, for instance by the exterior of the chamber being eroded away or ablated by sand or other abrasive substances, the now compromised chamber will see pressure very different from the static pressure in the chamber. This pressure will be close to the pressure in the well and thus could be much higher then the static pressure in the cavities of the erosion probe. The pressure differential will be sensed by the pressure transducers and generate the electrical signal useful in making people or equipment, including a computer based monitoring element, aware of the problem.

A second normally closed chamber may be used to augment the action of the first chamber. This chamber will operate in the same fashion as the first chamber but will provide a rate of wear measurement component to the system. When a second chamber and second pressure transducer system is used the time interval between the breach of the first chamber and breach of the second chamber will be recorded. The thickness of the material between the first chamber and the second chamber is known so given the time it takes to wear through this layer of material a simple algorithm can be solved to show the rate of wear. If the rate is fast the well can be immediately shut down. If the wear is slow then options to shut down or a controlled shut down can be accomplished.

A third advantageous element of the invention is that the erosion probe has a particular structure that exceeds the length of the conduit turning zone in an elbow. This enables the sensing of wear, erosion, or ablation over a larger area of the probe thus enabling the detection of wear over an area that intuitively would not be thought to be subject to erosion.

One other beneficial element of the invention is that the zone of detection is enhanced by means of the extended length of the cavities or chambers formed in the erosion probe.

BRIEF DESCRIPTION OF THE DRAWINGS

In the Drawing Figures:

FIG. 1 is an erosion detection device;

FIG. 2 is a partially sectioned view of a schematic representation of an erosion detection device;

FIG. 3 is an erosion probe component of the erosion detection device;

FIG. 4 is an end view of the device of FIG. 3;

FIG. 5 is a cross sectioned view through 5—5 of FIG. 3;

FIG. 6 is a cross sectioned view through 6—6 of FIG. 5;

FIG. 7 is a cross sectioned view through 7—7 of FIG. 3;

FIG. 8 is a cross sectioned view through 8—8 of FIG. 3.

DESCRIPTION OF THE PREFERRED EMBODIMENT

The invention will be understood by reading the following description of the preferred embodiment of the invention while purusing the drawing figures.

FIG. 1 is a presentation of the erosion detection device, generally 10. The device includes a probe section 12 and a transducer housing section 14 which is securely fastened to the probe section 12 by means of fasteners 16.

The flange portion 46 of the probe 12 is provided with fastener receiving through bores 22 that will facilitate attachment of the erosion detection device 10 to an erosion block. The generally cylindrical reactive zone 24 of the probe 12 is machined to form a complex arcuate surface forming a contact zone 26. Longitudinal through bores are formed in the probe 12 and in FIG. 1 a first and a second blocked lateral, 30 and 32 respectively, can be seen. These laterals are sealed with a plug, either welded or screwed in, and no pressure or fluid will pass these plugs when the probe is installed.

The protective housing, or transducer housing section 14 is a cavity containing structure having a cavity for containing and protecting a plurality of pressure transducers and attendant cabling. The pressure transducer wires are sheathed in an armored cable sleeve 64 attached by a waterproof fitting 40 to the protective housing. The fitting could, in an alternative embodiment exit from another location of the housing.

FIG. 2, a somewhat contrived and illustrative embodiment of the invention shown in FIG. 1, shows where the erosion probe and attendant protective housing will attach to an erosion block 40. The erosion block 40 is a machined block housing a radically angled or turned passage or tunnel 42 formed in the block 40. The passage will, in this application, allow the transmission of a flowable fluid, such as gas from a gas well or oil from an oil well, through the block 40. A bore 44 is also formed in the block 40. This bore 44 will intersect the passage 42 in the vicinity of the elbow or angled passage. In a preferred embodiment this bore 44 will have an interior diameter closely equivalent to the exterior diameter at the round portion of the probe section 12. The bore 44, however, will be formed such that at least a portion of it will extend into the open area of the passage 42 in the erosion block as clear from FIG. 2.

The probe portion 12 includes a flange 46 provided with the fastener receiving through bores 22 to receive stud and nut fastening means 50. The studs being screwed into the erosion block 40. Circumferential seal 52 helps seal the juncture between the erosion block 40 and the flange 46 of the probe section 12.

A transducer housing section 14 is attached by stud and nut fasteners such as 54 to the flange section 46 of the erosion detection device. The transducer housing section 14 has an interior cavity 56 which extends from the base of the transducer housing section to an orifice such as 60. This orifice 60 will accommodate a fitting 62 allowing connection of an armored cable sheath 64. The electrical wires 66 and 68 will be housed in this armored cable sheath and provide electrical connection from a first transducer 70 and from a second transducer 72 to a monitoring station (not shown).

These transducers, 70 and 72, will sense pressure increases in bores 74 and 76, respectively, of the probe section. That is, when pressure inside either of these bores increases the pressure transducers will send a signal to the monitor showing the existence of pressure in the relevant bore. Normally—that is when no wear has eroded the surface of the probe contact zone 26—the transducers will not register pressure in the bores. However, when the bores are exposed to the pressure in the passage 42 of the erosion block 40, resulting from ablation of the surface of the contact zone 26, the transducers will register pressure and trigger an electrical output signal to a monitoring station.

Flow of fluid through the passage 42 is in the direction of the arrow (A), that is, flow will be towards the surface or contact zone 26 generally perpendicular to the first bore extension 78 and the second bore extension 80 which communicate with first 74 and second 76 bores respectively through first 30 and second 32 laterals or cross drilled bores respectively. It is significant that each of the bores, cross drilled laterals and bore extensions are blocked to normally communicate only with the transducers 70 and 72.

The operation, in principle, of the erosion detection device, explained as well further on in this specification, can be learned from FIG. 2 even though it is something of a pictorial presentation. With the flow, normally a stream of gas, flowing in the direction "A" through the passage in the erosion block, its impingement on the contact surface 26 is generally non-destructive.

If the gas well malfunctions and abrasive material such as sand is carried with the high velocity stream of gas, the mixture of gas and sand will ablate the contact surface 26. Over time, sometimes over a short period of time, the abrasive mixture will erode or ablate the metal of the contact surface 26 to the degree that the first bore extension 78 will be exposed. This will cause a pressure increase in the first bore extension 78, the first bore 74 and a resultant signal being outputted from the presence transducer 70 which is in communication with the first bore 74. The signal from the transducer 70 will be directed to a monitoring station, which could be a computer terminal, for subsequent notification or action.

If there is significant sand contaminated gas flow through the passage 42 in the erosion block 40 more depth or material will be eroded or ablated from the contact surface 26. In the context of this application the "contact surface" is that surface that is or becomes exposed to the fluid flow either immediately or eventually. Eventually the second bore extension 80 will be breached. Like the breach or break through of the first bore extension 78, the breach or break through of this second bore extension 80 will cause the pressure in the second bore 76 to be sensed by the pressure transducer 72 and communicated by wire 66 to a monitoring station or computer terminal remote from the location of the erosion detection device.

The erosion block 40 is a part of a wellhead assembly that is used to control flow from a well. The probe section 12 and attached flange section 46 is a unified and replaceable element that is expected to be partially consumed in the performance of its function—determination of abrasive material in a gas stream by measuring the rate of erosion or ablation in a particular section of a wellhead.

In FIG. 2 another significant element of the invention is shown. This is the length of the contact zone 26. The contact zone 26 extends beyond the bend radius and the relative diameter of the passage 42 in the erosion block 40 so that it can sense erosion due to eddies and other flow dynamics that cause degradation of the passage surface downstream from the actual turn or elbow zone of the erosion block 40. The length is at least the diameter of the passage and may be a multiple thereof—say on the order of two or three times the conduit diameter. This extra length in the contact zone allows the detection of erosion beyond the fluid turning zone.

As mentioned above, FIG. 2 is a pictorial representation of the invention in the environment in which it operates. FIGS. 1 and 3 through 8 represent actual embodiments of the invention.

In FIG. 3 the probe section 12, having the flange portion 46, and the contact zone 26 is shown. In this embodiment several access ports 82, 30 and 32 are visible. These are blocked off cross drilled laterals used to provide pressure transmitting passages in the probe section 12. The lateral 82 is shown in FIG. 6 while the first blocked lateral 30 (plug welded and machined smooth) is shown in FIG. 7 and the second blocked lateral 32 (also plug welded and machined smooth) is shown in FIG. 8.

FIG. 4 shows the end view of the probe section with the flange 46 and the representative fastener receiving through bores such as 22 shown for reference. Significant in this view is the contact zone 26, the first bore extensions such as 78 and the second bore extensions 80. The first bore extension 78, one of five small bores aligned proximate to the edge of the contact zone 26 wall, are, in a preferred embodiment, 0.25 inches in diameter and approximately 9 inches deep aligned parallel to the major axis of the probe section. The second bore extension, 80, one of the four larger bores aligned relatively outboard of the array of first bore extensions, are, in a preferred embodiment, 0.50 inches in diameter and about 8 inches deep. Also shown in this view is communication port 84. Communication port 84 is a bore of 0.25 inches in diameter that is approximately 10 inches deep as measured, as are the first and second bore extensions, from the base of the probe section. This communication port 84 has been formed concentric with the second bore extension but is deeper.

The various ports are best seen in FIGS. 5-8. The FIG. 5 presentation is a cross section through 5—5 of FIG. 3 and shows the probe section 12, the first bore extensions 78, the second bore extensions 80 and the communication port 84.

FIG. 6 shows the probe section 12, a lateral 82 and the communication port 84. The first bore 74 is the bore from which the first transducer 70 will sense pressure. The second bore 76 is the bore from which the second transducer 72 will sense pressure which will be present in the communication port 84.

Turning to FIG. 7, a section through 7—7 of FIG. 3 the first bore 74 is shown in communication with the first bore extensions, one shown as 78. Thus pressure in the first bore extensions will be communicated to the first bore 74 and to the first transducer 70 through the first blocked lateral 30 and the first communication conduit 86.

Next turning to FIG. 8, the section through 8—8 of FIG. 3, the second bore extensions 80 are seen connected together by means of the second blocked lateral 32. If, as with the first bore extensions, any of the connected second bore extensions sees pressure then all of the second bore extension, and the second bore and the second pressure transducer 72 will see pressure. It should be pointed out that one of the second bore extensions 80, in this view it would be the second bore extension on the right side of FIG. 8, is connected to the communication port 84 and subsequently to the second bore 76 and the pressure transducer 72 as is shown in FIG. 6.

The operation of the erosion detection device depends on the generation of pressure, due to ablative wear or erosion of the surface of the contact zone 26. The pressure transducers 70 and 72 will cause an electrical signal to be generated and communicated to a remote monitor or operator's station. The presence of pressure detection by the first pressure monitoring labyrinth of the first bore 74 and the first bore extensions 74, and the generation of the pressure signal resulting from the transducer output, will be an indication that highly abrasive material, such as sand is in the flowing gas stream passing through the passage A in the erosion block. This abrasive fluid will wear through the surface metal of the contact zone 26 into one of the first bore extensions 78. When this occurs, the pressure transducers will register an increase in pressure, the absolute value thereof which may not be necessary, and cause the control panel to send a signal to the operator or do other activity such as recording the time of the pressure increase occurrence or even shutting down the well, as it may be programmed into the system. This sets a bench mark starting point in time from which the time to ablation of more material of the contact zone 26 can be measured.

If there is abrasive material, sand in a gas stream, that is being pumped from the well, and through or passed through the erosion block 40, then it is expected that the ablation of the contact zone 26 will continue.

The thickness of the contact zone 26 from its surface to the first bore extensions is "X" in FIG. 5 and the thickness of the contact zone 26 from its surface to the second bore extensions is "Y" also as shown in FIG. 5.

With the pressurization of the first bore extensions 78 recorded at a certain time, the "first time," the time for erosion or ablation of the contact zone 26 to the second bore extensions 80, the "second time" (occurring when there is a pressure break through recorded) will be finite. Thus, the time to ablate or erode the material represented by "Y" minus "X" divided by the thickness measurement of the contact zone from the first bore extension to the section bore extension will yield the rate of ablation. If this rate is fast—on the order of minutes—then the operator would shut the well down or take other appropriate action as the rapid rate of ablation would indicate sand or abrasives in the gas or fluid, a problem that could be corrected before more gas is extracted. If, on the other hand, the rate of erosion is slow—several hours elapsing after the signal from the first pressure transducer, then other options would be available to the well operator.

In summary, in the most simple embodiment of the invention, a detector means for the detection of abrasive material being carried by fluid passing through a wellhead is provided. It includes an erosion block having a passage therein and a bore intercepting the passage. A probe is inserted into the bore of the erosion block, this probe having a contact zone, with a surface, exposed to the passage when the probe is inserted in the bore. There is, as part of the probe, a first bore extension in the probe inboard of the surface of the contact zone. This first bore extension will communicate with a first bore. A first pressure transducer means is provided for sensing pressure in the first bore and in the first bore extension connected thereto. This pressure transducer provides an electrical output indicative of a change in pressure in the first bore and is electrically coupled to a means for responding to the electrical output of the first pressure transducer.

The foregoing description, when read in conjunction with a perusal of the drawing figures, shows how the implementation of an erosion detection system can be and is used to meet the objects of the invention. The following claims seek to protect the inventor's idea by claiming the erosion detector in a manner that captures the spirit of the invention. Minor deviations and nuances of the invention are contemplated as being covered by the following claims.

What is claimed is:

1. Detector means for the detection of abrasive material being carried by fluid passing through a wellhead comprising:

an erosion block having a passage therein and a bore intercepting said passage;

a probe for insertion into said bore of said erosion block, said probe having a contact zone, with a surface, exposed to said passage when said probe is inserted in said bore of said erosion block;

a first bore extension in said probe inboard of the surface of said contact zone;

a first bore in communication with said first bore extension;

a first pressure transducer for sensing pressure in said first bore and in the first bore extension connected thereto, said first pressure transducer providing an electrical output indicative of a change in pressure in said first bore; and means for responding to said electrical output of said first pressure transducer;

wherein said passage in said erosion block includes a bend in the zone of the passage intersecting said bore of the erosion block and said surface of the contact zone is exposed to said passage in the zone of the bend in said passage.

2. The invention in accordance with claim 1 wherein multiple first bore extensions are formed in said probe.

3. The invention in accordance with claim 2 wherein said multiple first bore extensions are inboard of said contact zone and spaced equidistant therefrom.

4. The invention in accordance with claim 2 wherein said detector means further comprises:

at least one second bore extension in said probe inboard of the surface of said contact zone;

a second bore in communication with said at least one second bore extension; and a second pressure transducer for sensing pressure in said second bore and in said at least one second bore extension connected thereto, said second pressure transducer providing an electrical output indicative of a change in pressure in said second bore.

5. The invention in accordance with claim 4 wherein multiple second bore extensions are formed in said probe, each second bore extension outboard of said multiply first bore extensions.

6. The invention in accordance with claim 5 wherein said multiple second bore extensions are inboard of said contact zone, relatively inboard of said multiple first bore extensions and spaced equidistant from said contact zone surface.

7. The invention in accordance with claim 6 wherein the lateral distance from said contact zone surface to said first bore extensions is of a given dimension and the lateral distance from said contact zone surface to said second bore extensions is of a second given dimension.

8. The invention in accordance with claim 7 wherein the difference between the given dimensions is known.

9. The invention in accordance with claim 8 wherein said abrasive material being carried by fluid passing through a wellhead will erode said contact surface and expose said first extension bore to the pressure in the well.

10. The invention in accordance with claim 9 wherein exposure of said first extension bore to the pressure in the well will trigger said first pressure transducer to output a signal to a monitoring station.

11. The invention in accordance with claim 10 wherein said signal generated by said first pressure transducer will trigger said monitoring station to record a clock time corresponding to initial triggering of said first pressure transducer.

12. The invention in accordance with claim 11 wherein said abrasive material being carried by fluid passing through a wellhead will erode said contact surface and expose said second extension bore to the pressure in the well.

13. The invention in accordance with claim 12 wherein exposure of said second extension bore to the pressure in the well will trigger said second pressure transducer to output a signal to a monitoring station.

14. The invention in accordance with claim 13 wherein said signal generated by said second pressure transducer will trigger said monitoring station to record a clock time corresponding to initial triggering of said second pressure transducer.

15. The invention in accordance with claim 14 wherein means for determining the rate of erosion of said contact surface of said probe comprises:

means for recording the point in time, said "first time," when said first extension is exposed to the pressure in the well;

means for recording the point in time, said "second time," when said second extension is exposed to the pressure in the well;

means for subtracting said first time from said second time to yield a time duration representing the time taken to erode the surface of the contact zone from said first bore extension to said second bore extension;

means for dividing the difference between the given dimensions by the time duration to yield a rate of erosion.

16. The invention in accordance with claim 1 wherein said probe contact zone extends into said passage of said block a distance at least equal to the major diametrical dimension of said passage.

17. The invention in accordance with claim 16 wherein said probe contact zone extends into said passage of said block a distance greater than the major diametrical dimension of said passage.

18. Detector means for the detection of abrasive material being carried by fluid passing through a wellhead comprising:

an erosion block having a passage therein and a bore intercepting said passage;

a probe for insertion into said bore of said erosion block, said probe having a contact zone, with a surface, exposed to said passage when said probe is inserted in said bore of said erosion block;

a first bore formed in said probe inboard of said surface;

a second bore formed in said probe inboard of said surface;

a first pressure transducer for sensing pressure in said first bore, said first pressure transducer providing an electrical output indicative of a change in pressure in said first bore;

a second pressure transducer for sensing pressure in said second bore, said second pressure transducer providing an electrical output indicative of a change in pressure in said second bore; and means for responding to said electrical outputs of said first and second pressure transducers.

* * * * *